(12) United States Patent
Manoux

(10) Patent No.: US 8,240,538 B1
(45) Date of Patent: Aug. 14, 2012

(54) TRUE MULTI-FIRE SURGICAL STAPLER WITH TWO-SIDED STAPLE DEPLOYMENT

(75) Inventor: Philipe R. Manoux, Oakland, CA (US)

(73) Assignee: Cardica, Inc., Redwood City, CA (US)

( * ) Notice: Subject to any disclaimer, the term of this patent is extended or adjusted under 35 U.S.C. 154(b) by 135 days.

(21) Appl. No.: 12/788,571

(22) Filed: May 27, 2010

Related U.S. Application Data

(60) Provisional application No. 61/182,630, filed on May 29, 2009.

(51) Int. Cl.
*A61B 17/072* (2006.01)

(52) U.S. Cl. .................... 227/178.1; 227/179.1

(58) Field of Classification Search ............... 227/178.1, 227/179.1, 180.1; 606/219
See application file for complete search history.

(56) References Cited

U.S. PATENT DOCUMENTS

| | | | |
|---|---|---|---|
| 3,581,551 A | 6/1971 | Wilkinson | |
| 3,650,453 A | 3/1972 | Smith, Jr. | |
| 3,675,688 A | 7/1972 | Bryan et al. | |
| 3,899,914 A | 8/1975 | Akiyama | |
| 3,955,581 A | 5/1976 | Spasiano et al. | |
| 4,086,926 A | 5/1978 | Green et al. | |
| 4,127,227 A * | 11/1978 | Green | 227/83 |
| 4,228,895 A | 10/1980 | Larkin | |
| 4,275,813 A | 6/1981 | Noiles et al. | |
| 4,475,679 A | 10/1984 | Fleury, Jr. | |
| 4,589,416 A | 5/1986 | Green | |
| 4,633,861 A | 1/1987 | Chow et al. | |
| 4,655,222 A | 4/1987 | Florez et al. | |
| 4,719,917 A | 1/1988 | Barrows et al. | |
| 4,762,260 A | 8/1988 | Richards et al. | |
| 4,969,591 A | 11/1990 | Richards et al. | |
| 4,978,049 A | 12/1990 | Green | |
| 5,156,315 A | 10/1992 | Green et al. | |
| 5,170,925 A | 12/1992 | Madden et al. | |
| 5,192,288 A | 3/1993 | Thompson et al. | |
| 5,307,976 A | 5/1994 | Olson et al. | |
| 5,413,272 A | 5/1995 | Green et al. | |
| 5,476,206 A | 12/1995 | Green | |

(Continued)

FOREIGN PATENT DOCUMENTS

EP  1238634  9/1994

(Continued)

OTHER PUBLICATIONS

Gong, Shao W., "Perfectly flexible mechanism and integrated mechanism system design", *Mechanism and Machine Theory 39* (2004), (Nov. 2004),1155-1174.

(Continued)

*Primary Examiner* — Rinaldi Rada
*Assistant Examiner* — Nathaniel Chukwurah
(74) *Attorney, Agent, or Firm* — Brian A. Schar

(57) ABSTRACT

One example of a surgical stapler may include a first staple holder, a second staple holder opposed to the first staple holder; a first feeder belt extending into the first staple holder, a second feeder belt extending into the second staple holder; and staples affixed to and frangibly separable from each feeder belt. Another example of a surgical stapler may include an anvilless end effector that in turn includes two opposed staple holders; at least one feeder belt extending into each staple holder, and staples frangibly affixed to each feeder belt.

8 Claims, 1 Drawing Sheet

U.S. PATENT DOCUMENTS

| | | | |
|---|---|---|---|
| 5,484,451 A * | 1/1996 | Akopov et al. | 606/139 |
| 5,540,375 A * | 7/1996 | Bolanos et al. | 227/178.1 |
| 5,547,117 A | 8/1996 | Hamblin et al. | |
| 5,553,765 A | 9/1996 | Knodel et al. | |
| 5,620,289 A | 4/1997 | Curry | |
| 5,630,541 A | 5/1997 | Williamson, IV et al. | |
| 5,655,698 A | 8/1997 | Yoon | |
| 5,662,260 A | 9/1997 | Yoon | |
| 5,690,269 A * | 11/1997 | Bolanos et al. | 227/176.1 |
| 5,692,668 A | 12/1997 | Schulze et al. | |
| 5,810,855 A | 9/1998 | Rayburn et al. | |
| 5,816,471 A | 10/1998 | Plyley et al. | |
| 5,855,311 A | 1/1999 | Hamblin et al. | |
| 5,871,135 A | 2/1999 | Williamson IV et al. | |
| 5,875,538 A | 3/1999 | Kish et al. | |
| 5,894,979 A | 4/1999 | Powell | |
| 5,918,791 A | 7/1999 | Sorrentino et al. | |
| 5,964,774 A | 10/1999 | McKean et al. | |
| 6,306,149 B1 | 10/2001 | Meade | |
| 6,391,038 B2 | 5/2002 | Vargas et al. | |
| 6,419,682 B1 | 7/2002 | Appleby et al. | |
| 6,592,597 B2 | 7/2003 | Grant et al. | |
| 6,602,252 B2 | 8/2003 | Mollenauer | |
| 6,716,232 B1 | 4/2004 | Vidal et al. | |
| 6,817,508 B1 | 11/2004 | Racenet et al. | |
| 6,843,403 B2 | 1/2005 | Whitman | |
| 7,025,747 B2 | 4/2006 | Smith | |
| 7,055,730 B2 | 6/2006 | Ehrenfels et al. | |
| 7,097,089 B2 | 8/2006 | Marczyk | |
| 7,111,768 B2 | 9/2006 | Cummins et al. | |
| 7,128,253 B2 | 10/2006 | Mastri et al. | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,258,262 B2 | 8/2007 | Mastri et al. | |
| 7,401,720 B1 | 7/2008 | Durrani | |
| 7,434,715 B2 | 10/2008 | Shelton, IV et al. | |
| 7,467,740 B2 | 12/2008 | Shelton, IV et al. | |
| 7,497,865 B2 | 3/2009 | Willis et al. | |
| 7,506,791 B2 | 3/2009 | Omaits et al. | |
| 7,517,356 B2 | 4/2009 | Heinrich | |
| 7,588,177 B2 | 9/2009 | Racenet | |
| 7,604,151 B2 | 10/2009 | Hess et al. | |
| 7,635,073 B2 | 12/2009 | Heinrich | |
| 7,635,373 B2 | 12/2009 | Ortiz | |
| 7,641,432 B2 | 1/2010 | Lat et al. | |
| 7,644,848 B2 | 1/2010 | Swayze et al. | |
| 2003/0120284 A1 | 6/2003 | Palacios et al. | |
| 2003/0236551 A1 | 12/2003 | Peterson | |
| 2005/0184121 A1 | 8/2005 | Heinrich | |
| 2006/0011699 A1 | 1/2006 | Olson et al. | |
| 2006/0041273 A1 | 2/2006 | Ortiz et al. | |
| 2006/0151567 A1 | 7/2006 | Roy | |
| 2006/0253143 A1 | 11/2006 | Edoga et al. | |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton, IV et al. | |
| 2007/0118163 A1 | 5/2007 | Boudreaux et al. | |
| 2007/0125828 A1 | 6/2007 | Rethy et al. | |
| 2007/0175950 A1 | 8/2007 | Shelton et al. | |
| 2008/0078807 A1 | 4/2008 | Hess et al. | |
| 2008/0272175 A1 | 11/2008 | Holsten et al. | |
| 2009/0065552 A1 * | 3/2009 | Knodel et al. | 227/180.1 |

FOREIGN PATENT DOCUMENTS

| | | |
|---|---|---|
| EP | 1464287 | 10/2004 |
| EP | 1736104 | 3/2009 |
| JP | 2005160933 | 6/2005 |
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparascopic surgical instruments", *Mechanism and Machine Theory 38*, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology 18*(9), (Nov. 2004),811-817.

Steichen, Felicien M., et al., "Mechanical Sutures in Surgery", *Brit. J. Surg. 60*(3), (Mar. 1973),191-197.

"Notification of Transmittal of the International Search Report and the Written Opinion of the International Searching Authority", PCT/US2008/075449.

"International Search Report", PCT/US2008/075449.

"Written Opinion of the International Searching Authority", PCT/US2008/075449.

"Cardica Microcutter Implant Delivery Device 510(k), Cover Sheet, Table 10.1, "Substantial Equivalence Comparison," and Section 12, "Substantial Equivalence Discussion"", (Oct. 18, 2010).

* cited by examiner

TRUE MULTI-FIRE SURGICAL STAPLER WITH TWO-SIDED STAPLE DEPLOYMENT

This application claims priority to U.S. Provisional Patent Application Ser. No. 61/182,630, filed on May 29, 2009, which is herein incorporated by reference in its entirety.

FIELD OF THE INVENTION

The invention generally relates to surgical staplers and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient. However, it can be difficult and/or time-consuming to located the surgical site after reinsertion. Further, the process of removing the endocutter from the patient after each use, replacing the cartridge, and then finding the surgical site again is tedious, inconvenient and time-consuming, particularly where a surgical procedure requires multiple uses of the endocutter.

In order to overcome these difficulties, Cardica, Inc. of Redwood City, Calif. has developed a true multi-fire endocutter that is capable of firing multiple times without the need to utilize single-use-cartridges. Such an endocutter is described in, for example, U.S. Patent Application Publication No. 2009/0065552, published on Mar. 12, 2009 (the "Endocutter Publication"), which is hereby incorporated by reference herein in its entirety.

BRIEF DESCRIPTION OF THE DRAWINGS

The use of the same reference symbols in different figures indicates similar or identical items.

DETAILED DESCRIPTION

Figure 1:
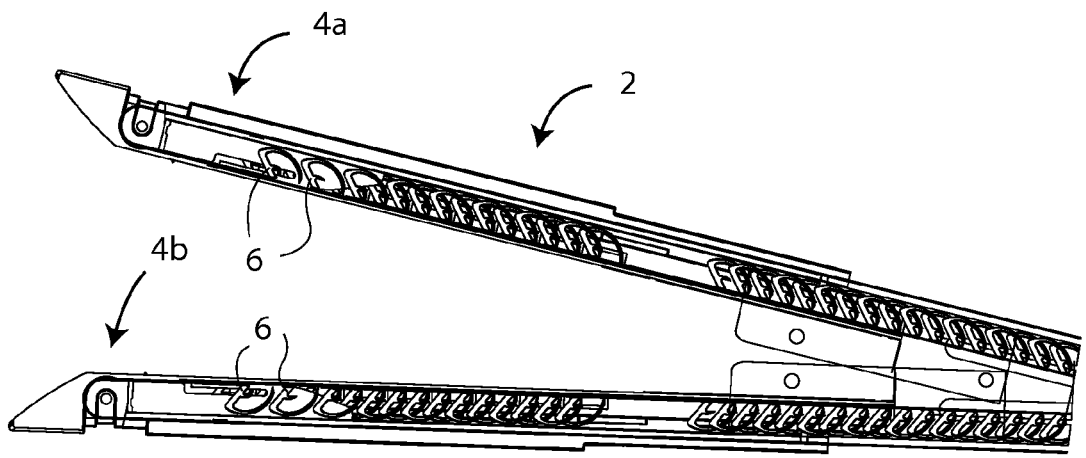
FIG. 1 is a cutaway side view of an endocutter in an open position, utilizing dual staple holders.
Figure 2:
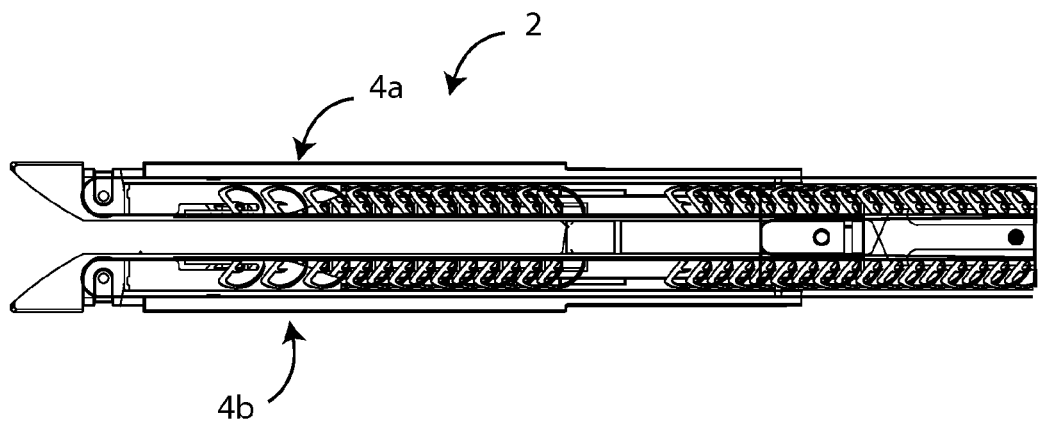
FIG. 2 is a cutaway side view of the endocutter of FIG. 1 in a closed position.

Referring to FIGS. 1-2, an end effector 2 of a surgical stapler may include two staple holders 4a, 4b, where at least one is movable relative to the other to compress tissue therebetween. For example, one or both of the staple holders 4a, 4b may be pivotable relative to the other. Each staple holder 4 may be configured substantially as described in the Endocutter Publication, and may be configured to deploy a plurality of staples that are fixed to and frangibly separable from at least one feeder belt substantially as described in the Endocutter Publication, with the following differences. The end effector 2 does not utilize a separate anvil; instead, staples 6 are deployed out of each staple holder 4 toward the other. Those staples 6 may be deformed and closed in any suitable manner. As one example, the staple holders 4a, 4b may be slightly offset relative to one another, and staple forming pockets may be defined in the surface of each staple holder 4a, 4b oriented toward the other. In this way, as staples 6 are ejected from one staple holder 4, those staples 6 encounter corresponding staple forming pockets on the surface of the other staple holder 4, causing those staples 6 to deform and close. The staple forming pockets are offset from apertures or other openings in the staple holder 4, such that deployment of staples 6 from one staple holder 4 toward the other, even at substantially the same time as deployment of staples 6 in the opposite direction from the other staple holder, does not result in interference between the staples 6 deployed from different staple holders 4. Alternately, the staple holders 4a, 4b need not be offset relative to one another to prevent interference between staples 6; instead, the apertures or other openings in one staple holder 4a may be offset from the corresponding apertures or other openings in the other staple holder 4b. Correspondingly, the feeder belt in each staple holder 4 may be configured differently from the feeder belt in the other staple holder 4 in order to deploy staples 6 from differently-positioned apertures. For example, one staple holder 4a may hold one or more feeder belts of a first width, where the staples 6 extend from the edges of each feeder belt, and the other staple holder 4b may hold one or more feeder belts of a second width that is less than the first width, where the staples 6 extend from the edges of each feeder belt. In this way, the staples 6 are offset without the need to offset the staple holders 4 themselves.

As another example of staple 6 deformation and closure, staples 6 deployed from one staple holder 4a may be deployed into contact with staples 6 from the other staple holder 4b intentionally. Opposed staples 6 may be deployed against one another, such that the staples 6 remain separate and independent after deployment and closure. Alternately, opposed staples 6 may be deployed into each other to create a single locking implant. If so, at least one staple 6 may include an aperture or other feature configured to receive the free end of an opposed staple 6 during deployment of those staples 6. Deployment of staples 6 from one staple holder 4a optionally may be timed differently than deployment of staples 6 from the other staple holder 4b, in order to deform or even completely close a staple 6 with an aperture or other interlocking feature outward first; as a result, the free end of the opposing staple 6 can then enter or otherwise engage that aperture or other interlocking feature during its deployment.

Deployment and closure of the staples 6 in each staple holder 4 may be substantially as set forth in the Endocutter Publication.

While the invention has been described in detail, it will be apparent to one skilled in the art that various changes and modifications can be made and equivalents employed, without departing from the present invention. It is to be understood that the invention is not limited to the details of construction, the arrangements of components, and/or the steps of performing anastomosis set forth in the above description or illustrated in the drawings. Therefore, the invention is not to be restricted or limited except in accordance with the following claims and their legal equivalents.

What is claimed is:
1. A surgical stapler, comprising:
a first staple holder;
a second staple holder opposed to said first staple holder;
at least a first feeder belt extending into said first staple holder;

at least a second feeder belt extending into said second staple holder; and a plurality of staples affixed to and frangibly separable from each said feeder belt;

further comprising staple forming pockets defined on the surface of said first staple holder, facing said second staple holder; and further comprising staple forming pockets defined on the surface of said second staple holder, facing said first staple holder.

2. The surgical stapler of claim 1, wherein said first feeder belt is advanceable within said first staple holder, and wherein said second feeder belt is advanceable within said second staple holder.

3. The surgical stapler of claim 1, wherein said first feeder belt and said second feeder belt are arranged relative to one another such that a plurality of said staples affixed to said first feeder belt contact a plurality of said staples affixed to said second feeder belt during deployment.

4. The surgical stapler of claim 1, wherein said first feeder belt and said second feeder belt are arranged relative to one another such that, during deployment, at least one said staple affixed to said first feeder belt contacts and interlocks with a corresponding said staple affixed to said second feeder belt.

5. The surgical stapler of claim 1, wherein said first feeder belt and said second feeder belt have different widths.

6. The surgical stapler of claim 1, wherein at least one said staple within said first staple holder is located at a different lateral position than at least one said staple within said second staple holder.

7. The surgical stapler of claim 1, wherein said first staple holder is offset relative to said second staple holder.

8. The surgical stapler of claim 1, wherein deployment of said staples from said first staple holder is timed differently from deployment of said staples from said second staple holder.

* * * * *